(12) United States Patent
Lumpkin et al.

(10) Patent No.: US 11,147,943 B1
(45) Date of Patent: Oct. 19, 2021

(54) VEHICLE NIGHTLIGHT ASSEMBLY

(71) Applicants: Demetrius Lumpkin, Laveen, AZ (US); Kimberly Lumpkin, Laveen, AZ (US)

(72) Inventors: Demetrius Lumpkin, Laveen, AZ (US); Kimberly Lumpkin, Laveen, AZ (US)

( * ) Notice: Subject to any disclaimer, the term of this patent is extended or adjusted under 35 U.S.C. 154(b) by 0 days.

(21) Appl. No.: 16/898,567

(22) Filed: Jun. 11, 2020

(51) Int. Cl.
*A61M 21/02* (2006.01)
*F21V 21/096* (2006.01)
*B60N 2/28* (2006.01)
*A61M 21/00* (2006.01)

(52) U.S. Cl.
CPC ......... *A61M 21/02* (2013.01); *F21V 21/0965* (2013.01); *A61M 2021/0044* (2013.01); *B60N 2/28* (2013.01)

(58) Field of Classification Search
CPC .. A61M 2/02; F21V 21/0965; F21V 21/0885; F21V 21/145; F21V 21/08; F21V 21/096; F21V 21/406
See application file for complete search history.

(56) References Cited

U.S. PATENT DOCUMENTS

| | | | |
|---|---|---|---|
| D376,662 S | 12/1996 | Ambrosio | |
| 6,039,455 A | 3/2000 | Sorenson | |
| 6,126,233 A | 10/2000 | Gaetano | |
| 6,149,489 A | 11/2000 | Johnson | |
| 7,201,444 B2 | 4/2007 | Schimmoller | |
| 8,113,579 B2 | 2/2012 | Fiore, Jr. | |
| D780,968 S | 3/2017 | Jun | |
| 2010/0301645 A1 | 12/2010 | Uwnawich | |
| 2012/0134141 A1* | 5/2012 | Wright | F21L 4/045 362/103 |

FOREIGN PATENT DOCUMENTS

EP 2433832 3/2010

* cited by examiner

*Primary Examiner* — Christine H Matthews

(57) ABSTRACT

A vehicle nightlight assembly for soothing a child in a vehicle includes a light emitting unit is positionable on a car seat for a child in a vehicle. The light emitting unit emits light at an intensity of no greater than 20.0 lumens. In this way the light emitting unit can soothe a child in the car seat while simultaneously avoiding negatively affecting night vision of a driver of the vehicle. A magnet is coupled to the light emitting unit. A disk is provided and the disk is positionable against an opposite side of the child car seat with respect to the magnet. In this way the magnet magnetically engages the disk for removably retaining the light emitting unit on the child car seat.

4 Claims, 5 Drawing Sheets

VEHICLE NIGHTLIGHT ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention

The disclosure relates to nightlight devices and more particularly pertains to a new nightlight device for soothing a child in a vehicle.

(2) Description of Related Art Including Information Disclosed Under 37 CFR 1.97 and 1.98

The prior art relates to nightlight devices including an infant observation mirror that is attachable to a vehicle to facilitate a driver to view a child. The prior art discloses a variety of child car seats that have light emitters integrated therein. The prior art discloses a light on an articulating arm that can be clamped to a child car seat. The prior art also discloses a bracelet that includes a plurality of light emitters and a magnetic clasp.

BRIEF SUMMARY OF THE INVENTION

An embodiment of the disclosure meets the needs presented above by generally comprising a light emitting unit is positionable on a car seat for a child in a vehicle. The light emitting unit emits light at an intensity of no greater than 20.0 lumens. In this way the light emitting unit can soothe a child in the car seat while simultaneously avoiding negatively affecting night vision of a driver of the vehicle. A magnet is coupled to the light emitting unit. A disk is provided and the disk is positionable against an opposite side of the child car seat with respect to the magnet. In this way the magnet magnetically engages the disk for removably retaining the light emitting unit on the child car seat.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
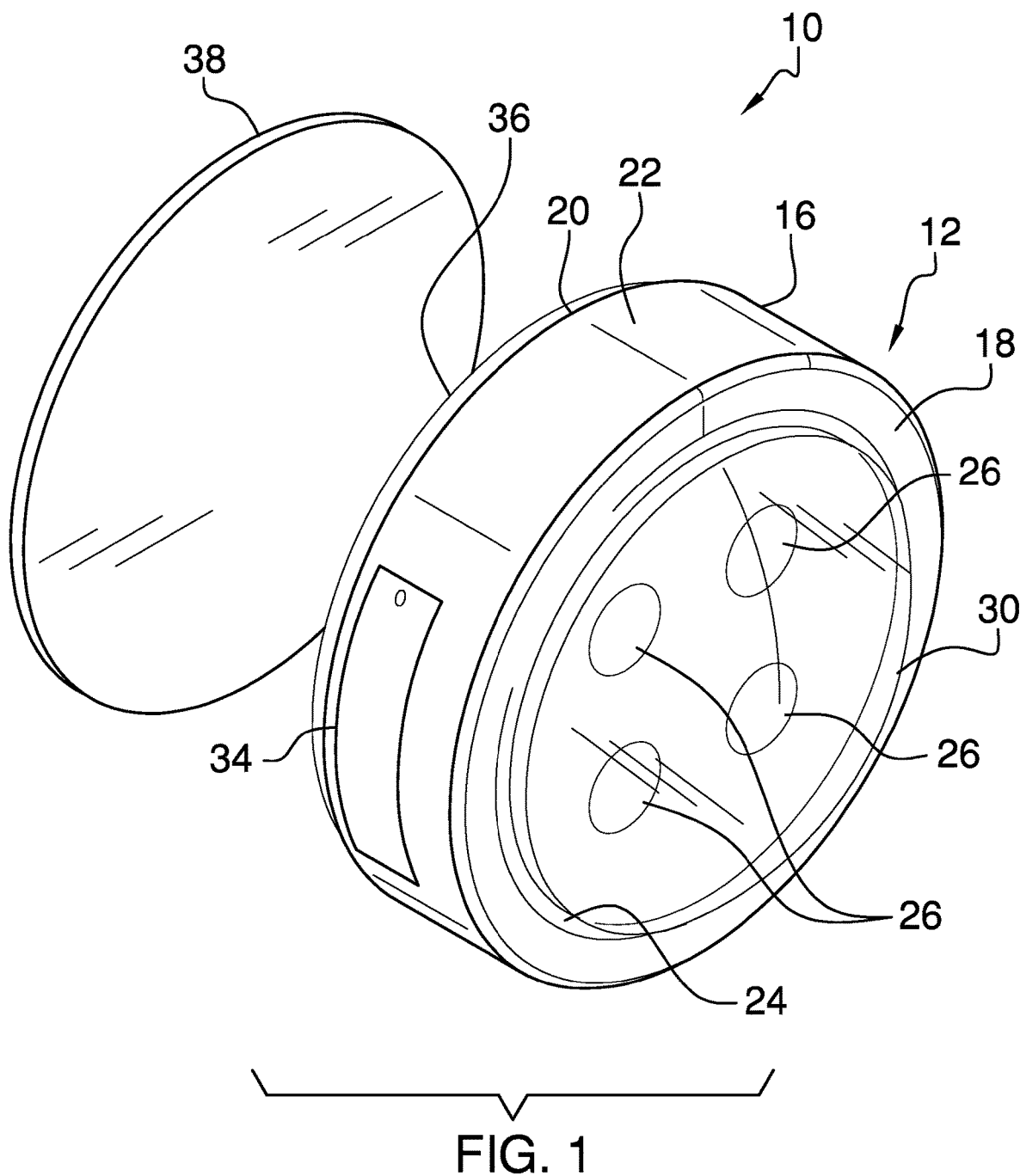
FIG. 1 is a front perspective view of a vehicle nightlight assembly according to an embodiment of the disclosure.
Figure 2:
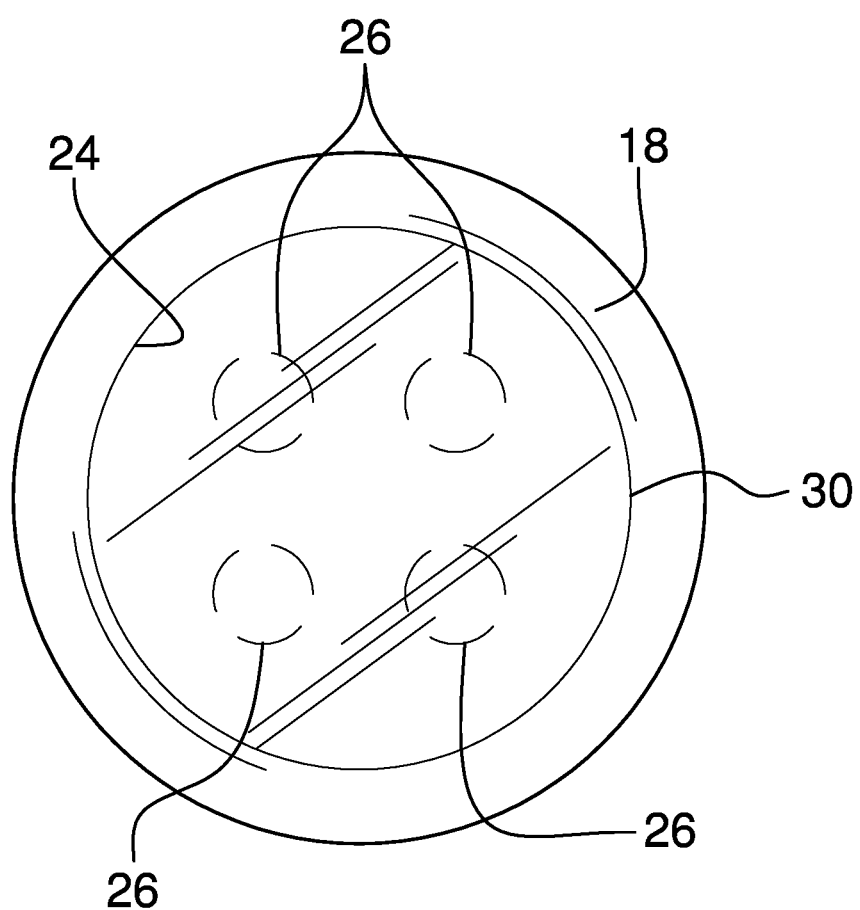
FIG. 2 is a front view of an embodiment of the disclosure.
Figure 3:
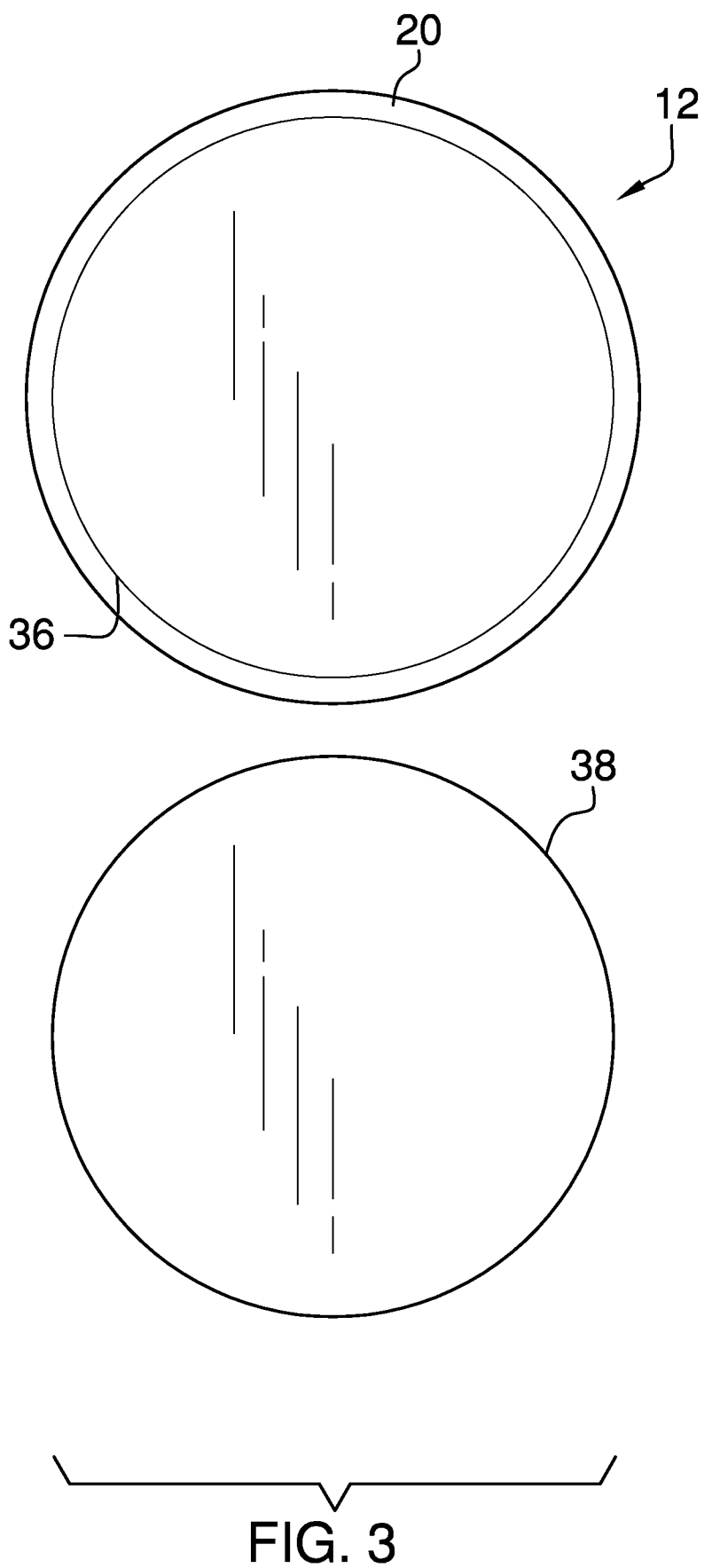
FIG. 3 is a back view of an embodiment of the disclosure.
Figure 4:
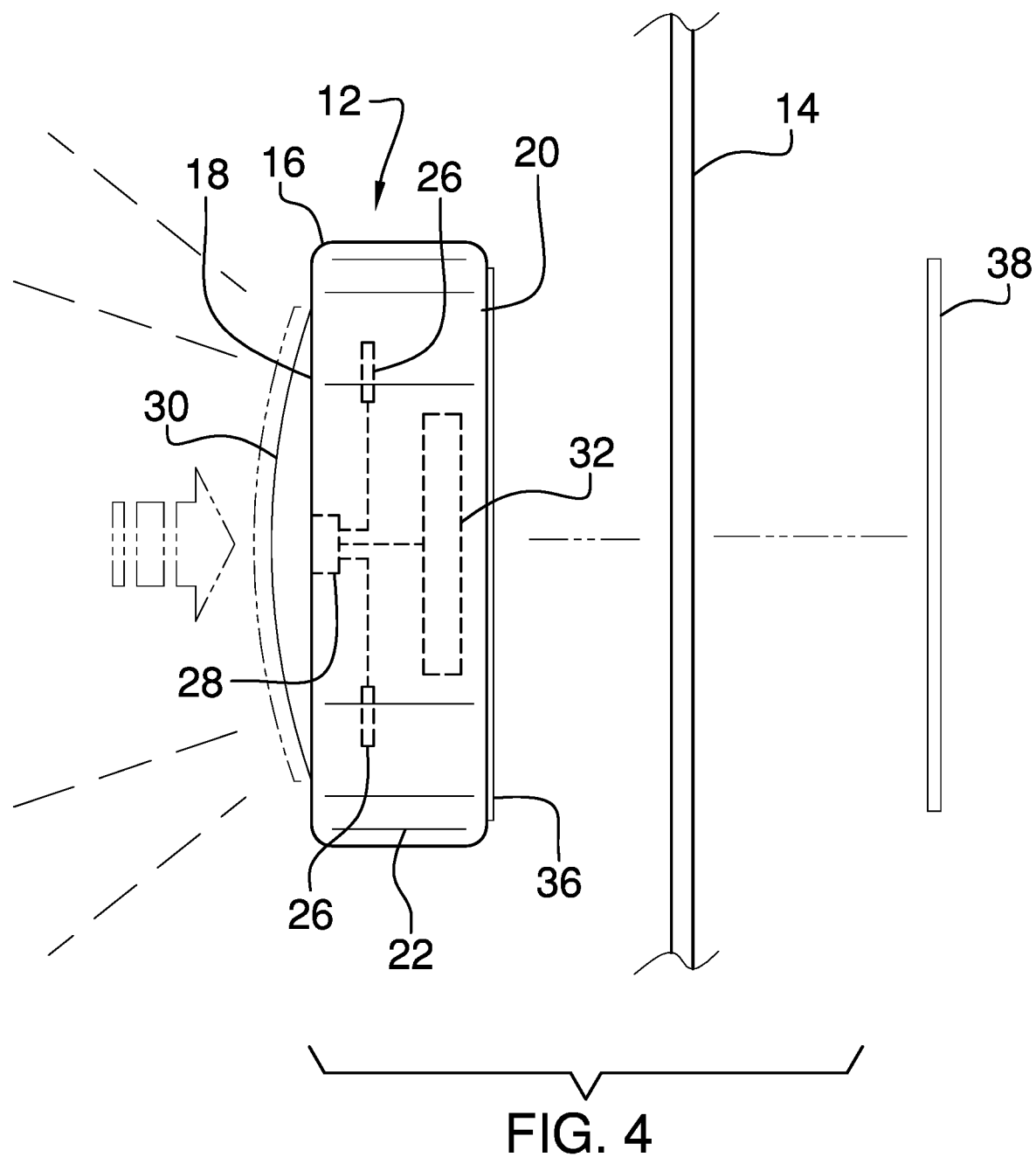
FIG. 4 is a left side view of an embodiment of the disclosure.
Figure 5:
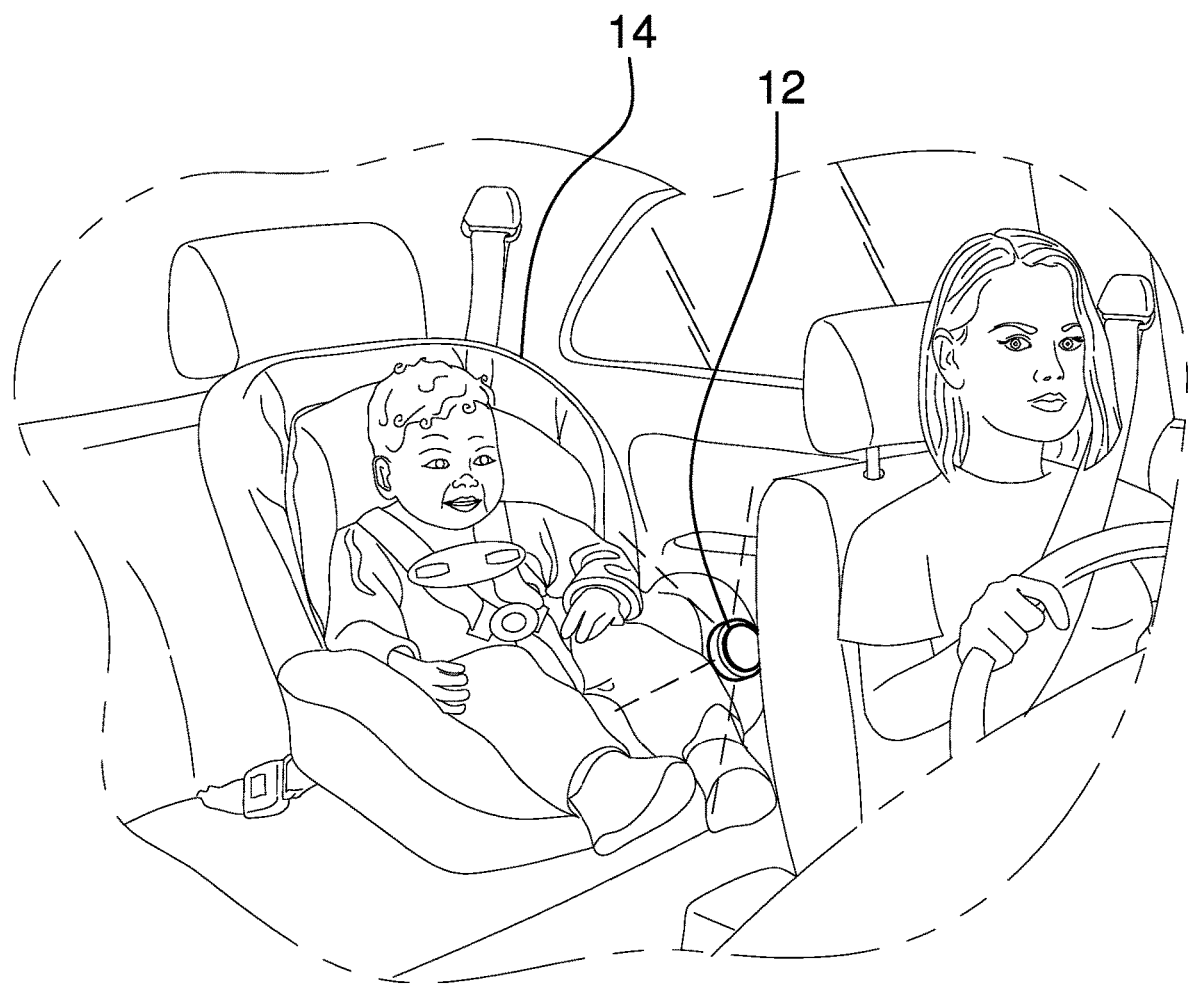
FIG. 5 is a perspective view of an embodiment of the disclosure.

With reference now to the drawings, and in particular to FIGS. 1 through 5 thereof, a new nightlight device embodying the principles and concepts of an embodiment of the disclosure and generally designated by the reference numeral 10 will be described.

As best illustrated in FIGS. 1 through 5, the vehicle nightlight assembly 10 generally comprises a light emitting unit 12 that is positionable on a child car seat 14 for a child in a vehicle. The light emitting unit 12 emits light at an intensity of no greater than 20.0 lumens. In this way the light emitting unit 12 soothes a child in the child car seat 14 while simultaneously avoiding negatively affecting night vision of a driver of the vehicle. The vehicle may be a passenger vehicle such as a car and the car seat may be a child safety seat of any conventional design.

The light emitting unit 12 comprises a housing 16 that has a front wall 18, a back wall 20 and an outer wall 22 extending therebetween, and the outer wall 22 is continuously arcuate about a center point of the front wall 18 such that the housing 16 has a disk shape. Additionally, the front wall 18 has an opening 24 extending into an interior of the housing 16.

The light emitting unit 12 includes a plurality of light emitters 26 that is each positioned within the housing 16 to emit light outwardly therefrom. Each of the light emitters 26 is aligned with the opening 24 in the front wall 18. Additionally, each of the light emitters 26 may comprise an LED or the like and each of the light emitters 26 may emit a continuously changing color of light. The light emitting unit 12 includes a switch 28 that is positioned within the housing 16. The switch 28 is electrically coupled to each of the light emitters 26 for turning the plurality of light emitters 26 on and off.

The light emitting unit 12 includes a lens 30 that is positioned over the opening 24 and the lens 30 is depressible into the opening 24. The lens 30 engages the switch 28 each time the lens 30 is depressed for turning the plurality of light emitters 26 on an off by depressing the lens 30. The lens 30 is comprised of a translucent material to pass light therethrough. The lens 30 is biased into a home position by a spring biasing member or the like such that the lens 30 returns to the home position each time the lens 30 is depressed. The light emitting unit 12 includes a power supply 32 is removably positioned in the housing 16 and the power supply 32 is electrically coupled to the switch 28. The power supply 32 comprises at least one battery and the power supply 32 is positioned beneath a battery cover 34 that is removably coupled to the outer wall 22 of the housing 16.

A magnet 36 is provided and the magnet 36 is coupled to the light emitting unit 12. The magnet 36 is positioned on the back wall 20 of the housing 16 and the magnet 36 is positionable against the child car seat 14. A disk 38 is positionable against an opposite side of the child car seat 14 with respect to the magnet 36 such that the magnet 36 magnetically engages the disk 38. In this way the light emitting unit 12 is retained on the child car seat 14. The disk 38 is comprised of a ferromagnetic material thereby facilitating the magnet 36 to magnetically engage the disk 38.

In use, the housing 16 is positioned against the child car seat 14 and the disk 38 is positioned against the child car seat 14 such that the magnet 36 magnetically engages the disk 38. In this way the housing 16 is retained on the child car seat 14. The lens 30 is depressed to turn on each of the light emitters 26. Thus, the light emitters 26 emit a gentle intensity of light to soothe the child. Additionally, the gentle intensity of light ensures that the driver's night vision is not compromised while driving.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A vehicle nightlight assembly for soothing a child while riding in a vehicle without distracting a driver of the vehicle, said assembly comprising:
    a light emitting unit being positionable on a car seat for a child in a vehicle, said light emitting unit emitting light at an intensity of no greater than 20.0 lumens wherein said light emitting unit is configured to soothe a child in the car seat while simultaneously avoiding negatively affecting night vision of a driver of the vehicle, wherein said light emitting unit comprises
        a housing having a front wall, a back wall and an outer wall extending therebetween, said outer wall being continuously arcuate about a center point of said front wall such that said housing has a disk shape, said front wall having an opening extending into an interior of said housing,
        a plurality of light emitters, each of said light emitters being positioned within said housing wherein each of said light emitters is configured to emit light outwardly therefrom, each of said light emitters being aligned with said opening in said front wall,
        a switch being positioned within said housing, said switch being electrically coupled to each of said light emitters for turning said plurality of light emitters on and off, and
        a lens being positioned over said opening, said lens being depressible into said opening, said lens engaging said switch each time said lens is depressed for turning said plurality of light emitters on an off by depressing said lens, said lens being comprised of a translucent material wherein said lens is configured to pass light therethrough;
    a magnet being coupled to said light emitting unit; and
    a disk being positionable against an opposite side of the child car seat with respect to said magnet such that said magnet magnetically engages said disk for removably retaining said light emitting unit on the child car seat.

2. The assembly according to claim 1, wherein said light emitting unit includes a power supply being removably positioned in said housing, said power supply being electrically coupled to said switch, said power supply comprising at least one battery, said power supply being positioned beneath a battery cover being removably coupled to said outer wall of said housing.

3. The assembly according to claim 1, wherein said magnet is positioned on said back wall of said housing, said magnet being positionable against the child car seat.

4. A vehicle nightlight assembly for soothing a child while riding in a vehicle without distracting a driver of the vehicle, said assembly comprising:
    a light emitting unit being positionable on a car seat for a child in a vehicle, said light emitting unit emitting light at an intensity of no greater than 20.0 lumens wherein said light emitting unit is configured to soothe a child in the car seat while simultaneously avoiding negatively affecting night vision of a driver of the vehicle, said light emitting unit comprising:
        a housing having a front wall, a back wall and an outer wall extending therebetween, said outer wall being continuously arcuate about a center point of said front wall such that said housing has a disk shape, said front wall having an opening extending into an interior of said housing;
        a plurality of light emitters, each of said light emitters being positioned within said housing wherein each of said light emitters is configured to emit light outwardly therefrom, each of said light emitters being aligned with said opening in said front wall;
        a switch being positioned within said housing, said switch being electrically coupled to each of said light emitters for turning said plurality of light emitters on and off;
        a lens being positioned over said opening, said lens being depressible into said opening, said lens engaging said switch each time said lens is depressed for turning said plurality of light emitters on an off by depressing said lens, said lens being comprised of a translucent material wherein said lens is configured to pass light therethrough; and a power supply being removably positioned in said housing, said power supply being electrically coupled to said switch, said power supply comprising at least one battery, said power supply being positioned beneath a battery cover being removably coupled to said outer wall of said housing;

a magnet being coupled to said light emitting unit, said magnet being positioned on said back wall of said housing, said magnet being positionable against the child car seat; and a disk being positionable against an opposite side of the child car seat with respect to said magnet such that said magnet magnetically engages said disk for removably retaining said light emitting unit on the child car seat, said disk being comprised of a ferromagnetic material thereby facilitating said magnet to magnetically engage said disk.

\* \* \* \* \*